US00PP21416P3

(12) United States Plant Patent
Ahrens

(10) Patent No.: US PP21,416 P3
(45) Date of Patent: Oct. 26, 2010

(54) *CUPRESSUS LEYLANDII* TREE NAMED 'MADELINE'

(50) Latin Name: *Cupressus leylandii*
Varietal Denomination: Madeline

(75) Inventor: Scott Ahrens, Clermont, FL (US)

(73) Assignee: Appaloosa Acres, Inc., Tampa, FL (US)

( * ) Notice: Subject to any disclaimer, the term of this patent is extended or adjusted under 35 U.S.C. 154(b) by 179 days.

(21) Appl. No.: 11/732,220

(22) Filed: Apr. 3, 2007

(65) Prior Publication Data

US 2008/0250536 P1 Oct. 9, 2008

(51) Int. Cl.
*A01H 5/00* (2006.01)

(52) U.S. Cl. ..... Plt./213

(58) Field of Classification Search ..... Plt./213
See application file for complete search history.

(56) References Cited

U.S. PATENT DOCUMENTS

PP11,217 P 2/2000 Greeves

*Primary Examiner*—Kent L Bell
(74) *Attorney, Agent, or Firm*—Gardner Groff Greenwald & Villanueva, PC

(57) ABSTRACT

A new and distinct cultivar of *Cupressus leylandii* tree is described herein. The new variety is resistant to fungus and possesses increased growth rate (e.g., height, spread, trunk) compared to the commercially-available Leyland Cypress 'Leighton Green'.

1 Drawing Sheet

Botanical denomination (Latin name): *Cupressus leylandii.*

Varietal denomination: 'Madeline'.

BACKGROUND

The Leyland Cypress (*Cupressus leylandii*) is a fast-growing evergreen tree used in horticulture. They are commonly planted as hedges or screens in gardens as a way to produce a boundary or create more privacy. Although Leyland Cyprus is a quick-growing plant, it has limitations. A major concern of the Leyland Cypress is its susceptibility to disease caused by fungus. For example, in regions with hot summers, Leyland Cyprus is very prone to the cypress canker caused by the fungus *Seridium cardinale*, which can ultimately kill the tree. Thus, it would be desirable to have a variety of Leyland Cypress that is more resistant to diseases caused by fungus as well as other favorable properties associated with Leyland Cypress. Described herein is a new cultivar of Leyland Cypress that addresses these needs.

SUMMARY OF THE INVENTION

The new cultivar of Leyland Cypress is a naturally occurring sport of 'Leighton Green', a commercially-available Leyland Cypress grown in a nursery in Newberry, Fla. The new cultivar was discovered as a naturally-occurring whole plant mutation. The new variety of Leyland Cypress named 'Madeline' was asexually reproduced in Leesburg, Fla. by rooting cuttings of Leyland Cypress in potted soil. Plants grown from the cuttings were subsequently planted in 5-gallon containers, with some plants grown in Sumterville, Fla. (USDA Hardiness level 9) and others grown in Cairo, Ga. (USDA Hardiness level 8). The plant cannot be reproduced true from seed. Three successive generations of the new cultivar have been asexually reproduced, and all of the cultivars have remained true to type.

Below is a list of distinguishing features of the new cultivar 'Madeline' described herein when grown under normal horticultural practices in Sumterville, Fla. and Cairo, Ga.

1. Resistant to diseases caused by fungus *Seridium cardinale.*
2. Increased height growth and spread growth.
3. Dark, attractive green color. The needle color is art green # 125 according to Maerz and Paul Dictionary of Color.
4. Needle tissue is thicker when compared to the commercially-available Leyland Cypress 'Leighton Green'. The scale like needle foliage emanating from the main branches has a larger needle diameter (approximately 10%) when compared to those of the needle thickness of 'Leighton Green'.
5. The needle-like leaves are farther apart from one another.
6. Increased rate of trunk caliper when compared to 'Leighton Green' (i.e., rate of trunk growth faster for cultivars of the present invention vs. 'Leighton Green').

As shown above, the new cultivar has a number of desirable features. In general, the new cultivar is resistant to fungus infestation when grown in Sumterville, Fla. and Cairo, Ga. In particular, the new cultivar is resistant to *Seridium cardinale* compared to 'Leighton Green'. This is a desirable feature in view of the susceptibility of commercially-available Leyland Cypress to fungus-causing diseases. The new cultivar also grows faster in height and spread growth by about 30% compared to other varieties of Leyland Cypress known to the inventor. Moreover, rate of trunk growth is faster by about 10% compared to other varieties of Leyland Cypress, which is indicative of a stronger root system typically not present in Leyland Cypress. In summary, the new cultivar is a robust plant that has many desirable features not present in known varieties of Leyland Cypress.

DESCRIPTION OF THE DRAWINGS

FIG. 1 is a photograph of *Cupressus leylandii* 'Madeline' in a 200 gallon container.

DETAILED PLANT DESCRIPTION

The following is a detailed description of the new cultivar based on observations of a seven year old specimen grown in a 200 gallon container at a nursery in Sumterville, Fla.

Form: Large, dense, and broadly pyramidal.

Height: Approximately 20'.

Width: Approximately 9'.

Trunk: Diameter between 5¼ and 5½ inches.

Needles: Dark green with spacing between needles of at least 0.1 cm farther apart compared to the commercially-available Leyland Cypress 'Leighton Green'.

Pests: None serious.

Branching in 8-9' tall trees in 15-gallon containers is composed of uniform lateral branching with observed branches every 4-5 cm growing at right angles from the trunk. At the trunk the diameter of the branch is 1 cm and the color of the branch is asphaltum #81 according to Maerz and Paul Dictionary of Color. The newer sections of the branch are alcanna #40. Branches are 65 long, stable, and have a strong cedar like fragrance.

What is claimed:

1. A new and unique variety of *Cupressus leylandii* tree named 'Madeline' as herein shown and described.

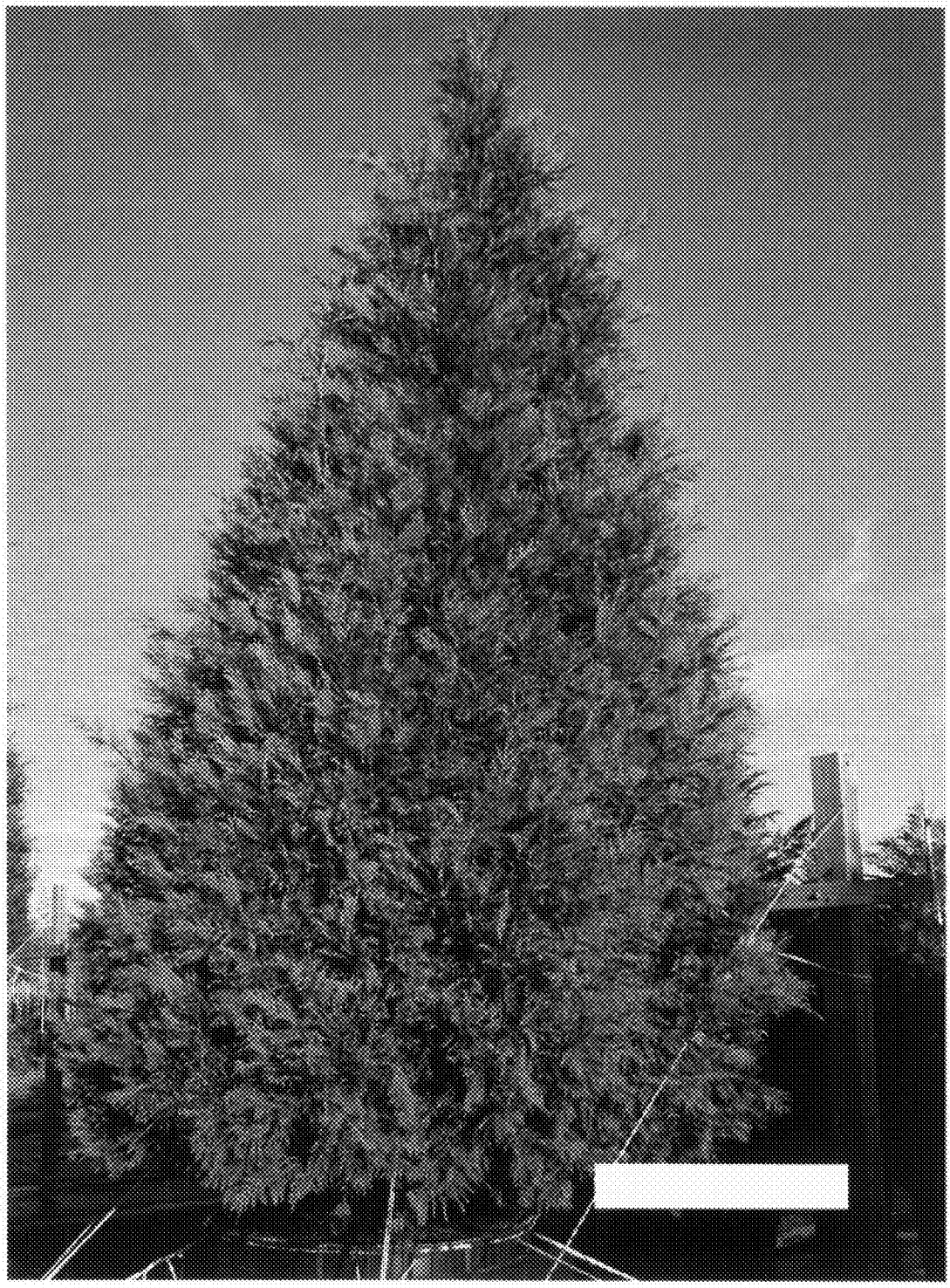

* * * * *